United States Patent
Rose et al.

(10) Patent No.: US 7,211,684 B2
(45) Date of Patent: May 1, 2007

(54) METHOD FOR PREPARING METHYL 2-DIPHENYLMETHYLSULFINYLACETATE

(75) Inventors: Sébastien Rose, Arsy (FR); Dominique Klein, Maurecourt (FR)

(73) Assignee: Cephalon France (FR)

( * ) Notice: Subject to any disclaimer, the term of this patent is extended or adjusted under 35 U.S.C. 154(b) by 0 days.

(21) Appl. No.: 10/541,527

(22) PCT Filed: Jan. 8, 2004

(86) PCT No.: PCT/IB2004/000002

§ 371 (c)(1),
(2), (4) Date: Oct. 27, 2005

(87) PCT Pub. No.: WO2004/063149

PCT Pub. Date: Jul. 29, 2004

(65) Prior Publication Data

US 2006/0235237 A1   Oct. 19, 2006

(30) Foreign Application Priority Data

Jan. 13, 2003 (EP) .................................. 03290082

(51) Int. Cl.
*C07C 321/00* (2006.01)
*C07C 331/00* (2006.01)
*C07C 239/00* (2006.01)

(52) U.S. Cl. .......................... 560/9; 560/311; 560/312; 564/162

(58) Field of Classification Search .................... 560/9, 560/311, 312; 564/162
See application file for complete search history.

(56) References Cited

U.S. PATENT DOCUMENTS

| 4,964,893 A | 10/1990 | Brannigan et al. ............ 71/88 |
| 5,571,825 A | 11/1996 | Boschelli et al. ........... 514/332 |

FOREIGN PATENT DOCUMENTS

| DE | 198 165 | 5/1908 |
| DE | 28 12 542 A1 | 10/1979 |
| GB | 1 584 462 | 2/1981 |
| WO | WO2004/063149 A1 | 7/2004 |

OTHER PUBLICATIONS

Carceller, E., et al., "Synthesis and structure-activity relationships of 1-Acyl-4-((2-methyl-3-pyridyl)cyanomethyl)piperazines as PAF antagonists," *J. Med. Chem.*, 1993, 36, 2984-2997.

Dahlbom, R., et al., "Diphenylmethoxyacetic acid and some related compounds," *Acta Chemica Scand.*, 1948, 2, 856-860.

du Roizel, B., et al., "Triisobutylaluminium promoted reductive rearrangement of substituted vinyl ethers to homologous alcohols," *Chem. Commun.*, 2000, 1507-1508.

Farinacci, N.T., et al., "Polymolecular solvolytic reactions: water catalysis in the alcoholysis of benzhydryl chloride," *J. Am. Chem. Soc.*, 1937, 59, 2542-2546.

Fujirebio, K.K., "Preparation of sulfenylacetic acids from alcohols and mercaptoacetic," *Jpn. Kokai Tokkyo Koho*, 1996, p. 11 (Abstract 1 page).

Fujita, S., et al., "Decarboxylative alkylation in the photolysis of benzhydryl esters," *Bull. Chem. Soc. Jpn.*, 1972, 45, 2571-2574.

Herzig, J., et al., "Uber Benzilsäure," *Ann. Chem.*, 1921, 422, 326-332 (German) (English abstract not available).

Iskander, Y., et al., "Carbon-Sulphur fission in thioethers. Part VI. The structural factors leading to either carbanion-sulphenium fission or α-proton extraction in p-nitrophenylmethylthio-acids," *J. Chem. Soc.*, 1961, 2397-2402.

Kumar, B., et al., "Iron (III) perchlorate: a reagent for transesterification," *Indian J. Chem.*, 1993, Sect. B, 292-293.

Lehr, H., et al., "Substituted 3-thiomorpholinones," *J. Med. Chem.*, 1962, 6, 136-141.

Lisac, S., et al., "Ferrocene compounds XXII. Synthesis and reactions of some ferrocenylthiaaliphatic acids," *J. Organomet. Chem.*, 1996, 507, 215-220.

Okarvi, S.M., et al., "Comparison of the labeling characteristics of mercaptoacetyltriglycine (MAG3) with different S-protective groups," *J. Labelled Compd. Radiopharm*, 1997, XXXIX (10), 853-874.

Parmar, A., et al., "Trans-esterification in dry media using ferric perchlorate adsorbed on silica gel," *Synth. Commun.*, 1999, 29(1), 139-143.

Saikawa, I., et al., "An efficient method for the preparation of 3-(substituted thiomethyl)-7-aminocephalosporins," *Chem. Pharm. Bull.*, 1985, 33(12), 5534-5538.

Schnurrenberger, P., et al., "Herstellung von methylestern durch umesterung funktionalisieter substrate mit titalsäureestern als katalysatoren," *Helv. Chim. Acta*, 1982, 65(4), 1197-1201 (English Summary).

Strazzolini, P., et al., "Nucleophilic substitution in diphenylmethyl derivatives. I. Formolysis of diarylmethyl derivatives: an α-substituent effect," *Recl. Trav. Chim., Pays-Bas*, 1991, 110, 5-12.

*Primary Examiner*—J. Parsa
(74) *Attorney, Agent, or Firm*—Woodcock Washburn LLP

(57) ABSTRACT

The invention relates to a method for preparing methyl 2-diphenylmethylsulfinylacetate (MDMSA) comprising the steps of: (i) conversion of benzhydrol into methyldiphenylmethylthioacetate (MDMTA); and (ii) conversion of methyldiphenylmethylthioacetate (MDMTA) into methyl-2-diphenylmethylsulfinylacetate by oxidation, according to the following sequence: benzhydrol→MDMTA→MDMSA.

31 Claims, No Drawings

METHOD FOR PREPARING METHYL 2-DIPHENYLMETHYLSULFINYLACETATE

CROSS-REFERENCE TO RELATED APPLICATIONS

This application represents entry into the U.S. national chase of International Application No. PCT/IB2004/000002, filed Jan. 8, 2004, which in turn claimed priority of European Application No. EP 03290082.1, filed Jan. 13, 2003.

FIELD OF THE INVENTION

The present invention relates to a novel method for preparing methyl 2-diphenylmethylsulfinylacetate (MDMSA).

BACKGROUND OF THE INVENTION

MDMSA is disclosed as an intermediate compound in the synthesis of modafinil also known as 2-[(diphenylmethyl)sulfinyl]acetamide. Modafinil which is a synthetic acetamide with wake-promoting activity, is useful in the treatment of narcolepsy, among other disorders.

The inventors have now discovered a novel route for synthesizing MDMSA which is applicable at the industrial scale.

Advantageously, the MDMSA can be obtained in two or three steps, each being characterized by high yields.

In an advantageous embodiment, these steps may be carried out in the same reactor and the same solvent, without isolating the intermediate compounds.

The aim of the present invention is to provide an economical and efficient method for preparing MDMSA.

SUMMARY OF THE INVENTION

These aims and others are achieved by the present invention which relates to a method for preparing methyl 2-diphenylmethylsufinylacetate comprising the steps of:
(i) conversion of benzhydrol into methyldiphenylmethylthioacetate; and
(ii) conversion of methyldiphenylmethylthioacetate into methyl-2-diphenylmethylsulfinylacetate by oxidation.

DETAILED DESCRIPTION OF PREFERRED EMBODIMENTS

Scheme 1 illustrates in general the steps used in this method:

Scheme 1

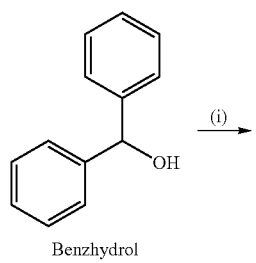

Benzhydrol

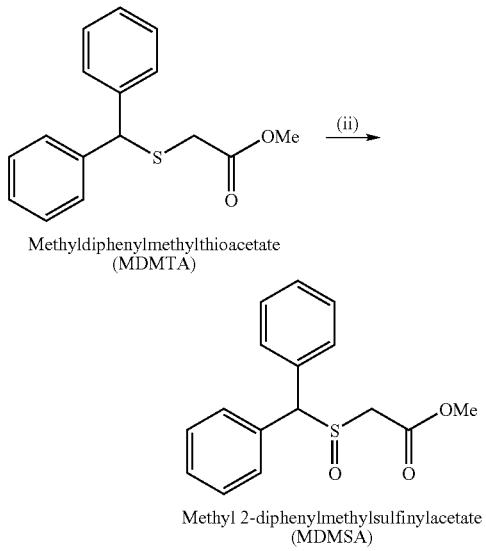

Methyldiphenylmethylthioacetate (MDMTA)

Methyl 2-diphenylmethylsulfinylacetate (MDMSA)

The reactions of steps (i) and (ii) used in this method are carried out in an appropriate solvent which may be easily chosen by persons skilled in the art, it being understood that an appropriate solvent denotes a solvent which is nonreactive towards the starting reagents, the intermediates or the products, at the reaction temperature considered, it being possible for the latter to vary from the solidification point of the solvent to the boiling point of the solvent.

A given reaction may be carried out in a solvent or in a mixture of several solvents, the solvent(s) being generally chosen according to the type of reaction considered and the subsequent treatment of the reaction medium.

In a preferred embodiment, the solvent is an aprotic solvent.

By way of illustration and without limitation of aprotic solvents which may be suitable for the method according to the invention, there may be mentioned in particular chlorinated solvents, aromatic solvents, hydrocarbon solvents and ethereal solvents.

Among the chlorinated solvents, chloroform, dichloromethane or chlorobenzene may be mentioned in particular.

Among the appropriate aromatic solvents, there may be mentioned, for example, benzene, toluene and chlorobenzene.

As examples of appropriate hydrocarbon solvents, cyclohexane, pentane and hexane may be mentioned.

Solvents such as diethyl ether, tetrahydrofuran and dioxane are useful as ethereal solvents.

Step (i) and (ii) may be conducted separately, notably in different solvents, where each intermediate is independently isolated.

In an advantageous embodiment, the reaction steps are conducted in the same reactor and without isolation of any intermediates.

Step i)

In a preferred embodiment, the conversion of benzhydrol into methyl diphenylmethylthioacetate comprises two steps of:
a1) conversion of benzhydrol into a benzhydryl carboxylate; and
b1) conversion of benzhydryl carboxylate into methyl diphenylmethyl thioacetate.

Scheme 2 illustrates in general steps a1) and b1) used in this method:

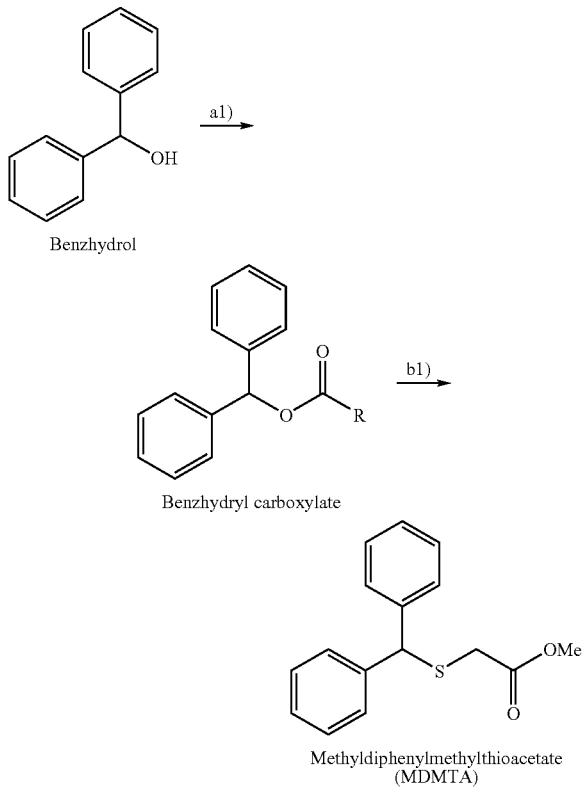

Step a1)

In one preferred embodiment, step a1) comprises reacting benzhydrol and an acid anhydride in the presence of an inorganic acid and in an appropriate solvent, preferably aprotic.

In the context of the present invention, dichloromethane is particularly preferred for its advantageous properties of extraction, distillation at low temperature, its nonflammability, its chemical neutrality and its capacity to be easily recycled in the context of this method.

Generally, the acid anhydride and the aprotic solvent are loaded simultaneously into the reactor, at a temperature of about 20° C.

The acid anhydrides for the purposes of the present description denote either symmetric anhydrides of monocarboxylic acids, mixed anhydrides, or cyclic anhydrides of polycarboxylic acids.

By way of examples of acid anhydrides which may be suitable in step a1) according to the invention, there may be mentioned in particular acetic anhydride, butyric anhydride and propanoic anhydride, acetic anhydride being particularly preferred.

The preferred reaction conditions are those which provide for the use of an equimolar quantity of acid anhydride relative to the benzhydrol in the aprotic solvent.

However, it is preferable to carry out the procedure in the presence of a slight excess of acid anhydride. An excessively high excess may indeed induce the formation of by-products in the subsequent steps of the method while an excessively small quantity is capable of slowing the kinetics of the oxidation reaction carried out in step (ii). Thus, the molar ratio of acid anhydride preferably varies between 1 and 1.2, even better between 1 and 1.1, and is advantageously 1.05, which corresponds to the optimum molar ratio of acid anhydride which makes it possible to obtain a clean synthesis.

Preferably, the procedure is carried out in the presence of a volume of solvent varying from 1.5 to 5 volumes, optimally in the presence of about 2 volumes. Under these conditions, the dilution brought about promotes the formation of the carboxylate.

According to an equally preferred variant of step a), the inorganic acid used is chosen from hydrochloric acid, hydrobromic acid, o-phosphoric acid and sulphuric acid, sulphuric acid being particularly preferred, in particular in the form of a 96% aqueous solution.

Preferably, the procedure is carried out in the presence of a quantity of inorganic acid ranging from 0.02 to 0.3 molar equivalents relative to the benzhydrol, even better from 0.05 to 0.15 equivalents.

As a safety precaution, the inorganic acid is generally introduced at a temperature of about 0° C. so as to control the exothermicity of the reaction.

The benzhydrol is then loaded at a sufficient temperature to allow a sufficiently rapid reaction kinetics, but not too high so as to avoid the formation of by-products such as benzhydryl ether. It is particularly preferable to carry out the procedure at a temperature of between −5° C. and +5° C., even better between −2° C. and +2° C. for an introduction time ranging from 45 minutes to 2 hours, preferably in about 1 hour. This introduction time indeed makes it possible to control the exothermicity of the reaction and to limit the formation of by-products.

The benzhydrol is generally maintained at this temperature for a sufficient contact time to obtain a complete reaction, but not too high in order to avoid the degradation of the benzhydryl carboxylate. The expression "complete reaction", for the purposes of the present invention, is understood to mean a reaction leading to the production of the derived product with a conversion rate greater than 99.2%, and preferably greater than 99.5%. In general, a complete reaction is obtained after a contact time of 2 hours.

The benzhydryl carboxylate obtained can be immediately used in the next step, without intermediate isolation.

Step a1) can also be realized by any other appropriate method.

As an example, step a1) can be realized by reacting benzhydrol with a carboxylic acid, for instance:

2-methyl-butyric acid in combination with:
  $SOCl_2$, pyridine, in benzene; or
  $H_2SO_4$ in dichloromethane; or
  TsOH in benzene as disclosed in the reference: Fujita S. and al., Bull. Chem. Soc. Jpn 1972, 45: 2571–2574;
  or acetic acid in combination with potassium iodide as described in Strazzoli P. et al., Recl. Trav. Chim., The Netherlands, 1991; 1:5–12.

By way of example, step a1) can also be realized by reacting a carboxylic acid salt, for instance acetic acid sodium salt as disclosed in Herzig S., Justus Liebigs, Ann. Chem.; 1921; 422:330.

By way of example, step a1) can also be realized by reacting benzhydrol with a carboxylic acid chloride, as for example acetyl chloride in the presence of triethylamine as disclosed in Roizel B. and al., Chem. Commun., 2000, 16:1507–1508.

As an example, step a1) can also be realized by reacting benzhydrol with acetic acid ethyl ester in the presence of Ti(OC$_2$H$_5$) (Schnurrenberger P. and al., Helv. Chim. Acta, 1982, 65(4): 1197–1201); or of iron (III) perchlorate (ITP) (Kumar B. and al., Indian J. Chem. Sect. B, 1993, 32(2): 292–293); or of Fe(ClO$_4$)$_3$, SiO$_2$ (Parmar and al., Synth. Commun., 1999, 29(1): 139–144).

Step b1)

Step b1) can be performed by any appropriate method.

In a preferred embodiment, step b1) comprises bringing the solution obtained in step a1) into contact with methyl thioglycolate.

The methyl thioglycolate is generally introduced in about 10 minutes at 0° C. but with no temperature restriction (it can then increase to about 9° C.). The reaction medium is then heated to a sufficiently high temperature to drive the reaction kinetics, but not too high so as to avoid the formation of by-products. Generally, the procedure is carried out at a temperature of between 15° C. and 25° C., preferably between 18° C. and 22° C., and contact is maintained at this temperature for a sufficient time to obtain complete reaction, with few by-products, generally for 2 to 3 hours, preferably for a period of 2 hours.

The methyl diphenylthioacetate can be used in step (ii) without intermediate isolation.

In another preferred embodiment, step i) comprises two steps of:
a2) conversion of benzhydrol into benzhydryl carboxylic acid;
b2) conversion of benzhydryl carboxylic acid into methyl diphenylmethylthioacetate.

This method is illustrated by scheme 3:

Step a2)

Step a2) may be realized according to any appropriate method and notably according to conditions disclosed in: Dahlbom O., Acta Chem. Scand., 1948, 2: 856–858; Carceller E. et al., J. Med. Chem., 1993; 36: 2984–2997; Lisac S. et al., J. Organomet. Chem. 1996, 507: 215–220; Okarvi S. et al., J. Labelled Compd. Radiopharm. 1997, 39: 853–874; Patent Thomae GmbH DE 2812542, 1979, Chem. Abstract 1980; 92; 198165; Iskander, Y. et al., J. Chem. Soc., 1961, 2397–2402.

In a particular embodiment, step a2) is realized by reacting benzhydrol with thioacetic acid, in the presence of an organic or inorganic acid.

Preferably, the solvent is a protic solvent, more preferably a carboxylic acid and notably acetic acid.

Inorganic or organic acid is preferably chosen among hydrochloric acid, POCl$_3$, trifluoroacetic acid, hydrobromic acid, o-phosphoric acid, sulphuric acid, POCl$_3$ and trifluoroacetic acid being particularly preferred.

Preferably, the reaction is realized at room temperature.

Step b2)

Esterification reaction of step b2) may be realized by any methods known from the person skilled in the art.

In another particular embodiment, step (i) comprises two steps of:
a3) conversion of the hydroxyl group of benzhydrol into a leaving group;
b3) conversion of the obtained product into methyldiphenylmethylthioacetate.

This method is illustrated by scheme 4:

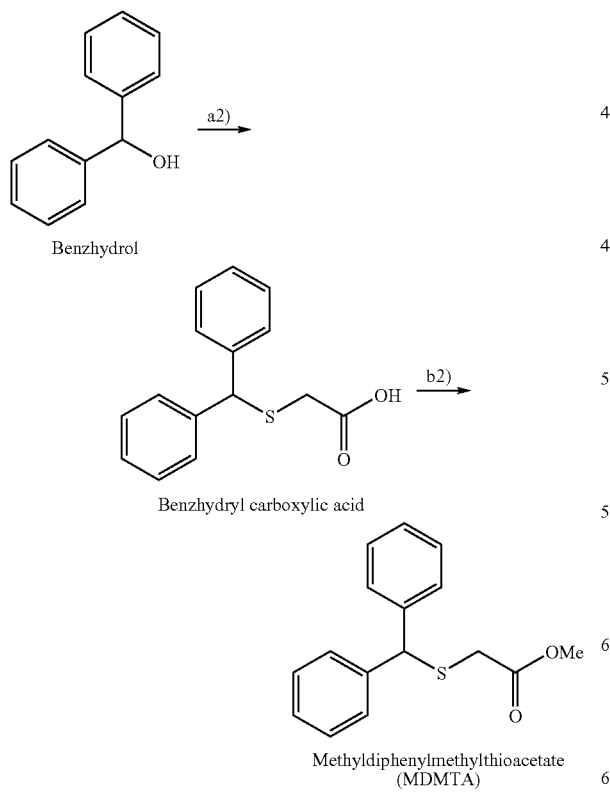

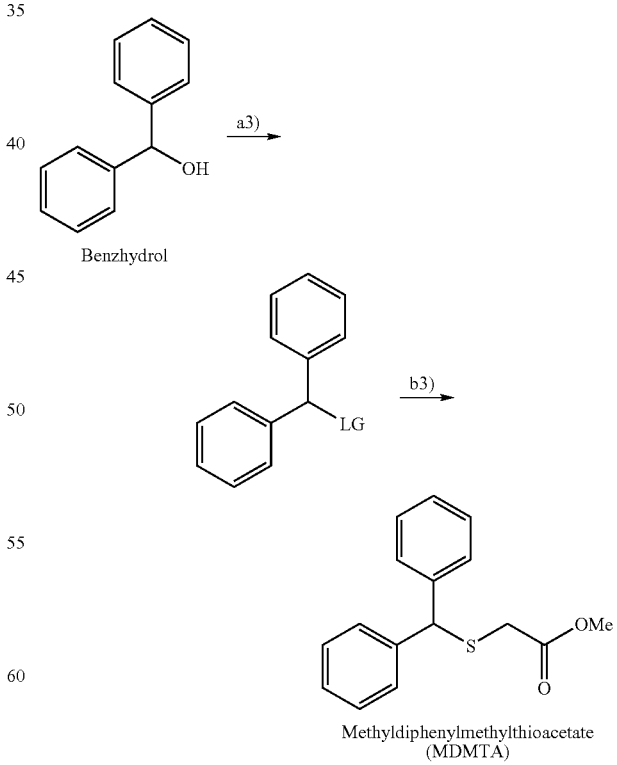

"LG" = leaving group

Step a3)

The leaving group in step a3) means any group that can be removed easily by a nucleophilic reactant. Leaving groups may be selected from the group consisting of halogenes, such as chloro- and bromo-radicals, or sulfonyl groups such as methanesulfonyl- or p-toluenesulfonyl-radicals.

Step a3) may be realized by any methods known from the person skilled in the art.

As an example, hydroxyl group of benzhydrol may be converted into chloro- or bromo-radical by reacting benzhydrol with thionyl choride or thionyl bromide.

As an example, hydroxyl group of benzhydrol may be converted into methanesulfonate group or into p-toluenesulfonate group by reacting benzhydrol respectively with methanesulfonyl chloride or p-toluenesulfonyl chloride.

Step b3)

In a preferred embodiment, step b3) is realized according to conditions of step b1).

Step b3) may also be realized by any other appropriate method.

In another preferred embodiment, step i) comprises reacting benzhydrol with methylthioglycolate in the presence of a metallic catalyst in a solvent, as illustrated by scheme 5:

Scheme 5

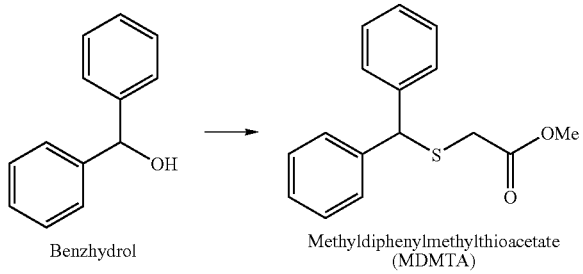

Benzhydrol → Methyldiphenylmethylthioacetate (MDMTA)

Preferably, the metallic catalyst is chosen from $ZnCl_2$, $ZnBr_2$, $ZnI_2$, $ZnI_2$ being particularly preferred.

Preferably, the solvent is chosen from aprotic solvents, more preferably from halogenated solvent and particularly chlorinated solvents such as dichloromethane, dichloroethane.

Step ii)

Inventors have now settled oxidation conditions that allow interestingly to control the conversion of methyldiphenylmethylthioacetate into methyl-2-diphenylmethylsulfinylacetate, notably formation of by-products, yields and kinetics of the reaction.

Various parameters used in step (ii) capable of influencing the efficiency of the reaction may be optimized, such as the quantity of oxidizing agent introduced, the dilution of the reaction medium, the reaction temperature, the contact time and the acidity of the reaction medium.

Thus, in general, an excessively small quantity of oxidizing agent means an incomplete reaction. Conversely, an excessively large excess promotes the formation of the dioxidized by-product, sulfone.

By way of illustration of oxidizing agents which may be suitable for the invention, there may be mentioned in particular oxone, potassium permanganate, sodium percarbonate, peroxides such as hydrogen peroxide, tert-butyl hydroperoxide and m-chloroperoxybenzoic acid, hydrogen peroxide being particularly preferred.

In a preferred embodiment, step ii) is performed in dichloromethane.

According to a preferred embodiment, the oxidizing agent used in step (ii) is hydrogen peroxide, preferably in the form of a 35% aqueous solution. Indeed, a lower titre causes a higher dilution, which can decrease the kinetics of the reaction.

Although a stoichiometric quantity of oxidizing agent is sufficient, it is preferably to carry out the procedure in the presence of a slight excess, preferably in the presence of a molar ratio of between 1 and 1.1.

The acidity of the medium results from the operating conditions of step (i).

The reaction temperature can influence the kinetics of the oxidation reaction. Thus, it is preferable that the temperature is between 28° C. and 37° C., the temperature range for which the reaction kinetics is particularly increased taking into account the acidity of the medium.

Preferably, a reaction temperature of between 28° C. and 32° C. is preferred. This temperature indeed makes it possible to have optimum control of the method, in particular the stopping point beyond which superoxidation becomes non-negligible.

The contact time in order to obtain a clean and complete reaction may vary according to the scale of operation and also according to the quantity of inorganic acid, in particular of sulfuric acid, present in the reaction medium at step b).

Preferably, the reaction is considered as being "complete" in step (ii) when the ratio $R_1$=nonoxidized derivative/(monooxidized+dioxidized+nonoxidized derivative)<0.5%.

The expression "clean" reaction is understood to mean, for the purposes of the present description, a reaction in which the ratio $R_2$=dioxidized derivative/(monooxidized+dioxidized+nonoxidized derivative)<0.5%.

The contact time necessary in order to obtain a clean and complete reaction may be determined using conventional analytical techniques which make it possible to monitor the progress of the reaction, such as HPLC (High-Performance Liquid Chromatography), IR (Infrared) or NMR (Nuclear Magnetic Resonance).

In general, the contact time necessary and sufficient to obtain a clean and complete reaction is less than 35 hours, preferably less than or equal to 33 hours, so as to avoid the formation of by-products such as in particular diphenylmethylthioacetic acid, and greater than 20 hours, preferably greater than or equal to 25 hours.

Of course, it is within the capability of persons skilled in the art to adjust the contact time necessary for obtaining a complete reaction at the scale of operation considered.

An increase in the quantity of inorganic acid in the reaction medium can nevertheless make it possible to significantly reduce the oxidation reaction time.

Without wishing to be limited to any theory, a hypothesis which makes it possible to explain this unexpected effect is that the inorganic acid plays a catalyst role in the mechanism of oxidation by the oxidizing agent. By way of example, in the case of sulphuric acid, it is assumed that a reaction intermediate of the $H_2SO_5$ type is formed in the medium, transferring oxygen either directly to the oxidizable species, or indirectly by an accelerated formation of peracetic acid.

Thus, according to a preferred variant of step (ii) of the method according to the invention, an additional quantity of inorganic acid, preferably of 0.02 to 0.3 molar equivalents, and more preferably of 0.05 to 0.15 molar equivalents is added to the reaction medium in step b1), generally prior to the introduction of the oxidizing agent. An acceleration of the reaction kinetics is then observed.

Advantageously, the contact time required which is sufficient to obtain a complete and clean reaction in step (ii) is considerably reduced and is generally between 10 and 13 hours.

Advantageously, the introduction of the inorganic acid in two portions makes it possible to reduce the acidity of the reaction medium in steps a1) and b1) and therefore to limit the formation of by-products.

Step (iii)

In a further embodiment, the method according to the invention comprises an additional step of iii) recovering the methyl 2-diphenyl-methylsulfinylacetate obtained.

The isolation of the MDMSA formed in step (iii) can be carried out according to any conventional method known to persons skilled in the art.

Preferably, the MDMSA is isolated by extraction.

The organic phases are then combined and concentrated under reduced pressure, preferably at a temperature of 70° C.

According to a particular variant, the solvent is distilled to dryness.

The product may be purified according to any method known to persons skilled in the art such as recrystallization or chromatography.

According to a particular embodiment, step (iii) may comprise a step of direct crystallization of the MDMSA.

The expression "direct crystallization", for the purposes of the present description, is understood to mean a crystallization of the noncrystallized product caused by the addition of appropriate solvents, preferably chosen in particular from methanol, ethanol, ethyl acetate, isopropyl acetate and toluene, isopropyl acetate being particularly preferred.

In this context, the crystallization solvent is introduced after substantial removal of the aprotic solvent.

Advantageously, this direct crystallization makes it possible to purify the crude product immediately in the remainder of the method and thus to dispense with an isolation step and a more costly subsequent retreatment step.

In a particularly preferred embodiment, the method comprises the steps of:
  i) a1) converting benzhydrol into a benzhydryl carboxylate by reacting benzhydrol and an acid anhydride in the presence of an inorganic acid and in an appropriate aprotic solvent;
  b1) converting the benzhydryl carboxylate into methyl diphenylmethylthioacetate by bringing the above solution into contact with methyl thioglycolate;
  ii) converting the diphenylmethylthioacetate into methyl 2-diphenylmethylsulfinylacetate by bringing the above solution into contact with an oxidizing agent;
  and optionally;
  iii) recovering the methyl 2-diphenylmethylsulfinylacetate obtained.

This embodiment is illustrated by scheme 6:

Scheme 6

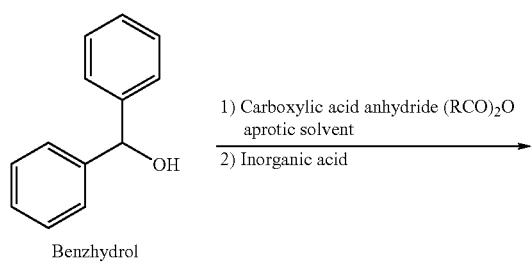

Benzhydrol

1) Carboxylic acid anhydride (RCO)$_2$O aprotic solvent
2) Inorganic acid

-continued

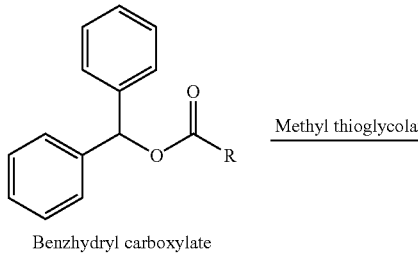

Benzhydryl carboxylate

Methyl thioglycolate

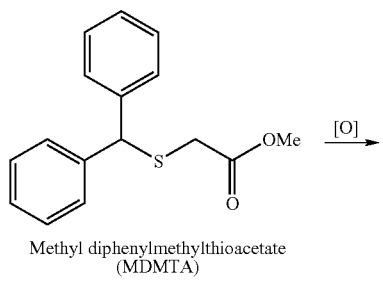

Methyl diphenylmethylthioacetate (MDMTA)

[O]

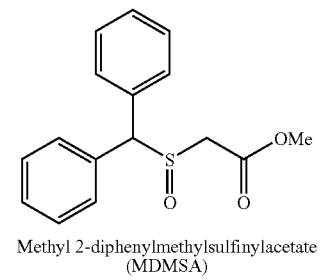

Methyl 2-diphenylmethylsulfinylacetate (MDMSA)

Advantageously, the MDMSA is obtained in three successive steps, each being characterized by high yields.

Furthermore, these three steps may be carried out in the same reactor and the same solvent, without isolating the intermediate compounds.

Advantageously, the formation of undesirable by-products is limited and controlled according to this method, which makes it possible to dispense with subsequent reprocessing steps.

Finally, according to another advantageous aspect, this method makes it possible to reduce the costs of manufacturing MDMSA, in particular because of its ease of use, and its high productivity and reproducibility.

The present invention also aims at the MDMSA obtained by the method of the invention and particularly by the method implementing:
  i) a1) converting benzhydrol into a benzhydryl carboxylate by reacting benzhydrol and an acid anhydride in the presence of an inorganic acid and in an appropriate aprotic solvent;
  b1) converting the benzhydryl carboxylate into methyl diphenylmethylthioacetate by bringing the above solution into contact with methyl thioglycolate;
  ii) converting the diphenylmethylthioacetate into methyl 2-diphenylmethylsulfinylacetate by bringing the above solution into contact with an oxidizing agent;
  and optionally;
  iii) recovering the methyl 2-diphenylmethylsulfinylacetate obtained.

The present invention is also directed to a method for preparing modafinil comprising the steps of:
(i) conversion of benzhydrol into methyldiphenylmethylthioacetate; and
(ii) conversion of methyldiphenylmethylthioacetate into methyl-2-diphenylmethylsulfinylacetate by oxidation.

EXAMPLES

Example 1

Synthesis of MDMSA on the Laboratory Scale (0.5 l)

a) Benzhydryl Acetate 108.3 g (1.05 mol; 1.05 eq) of acetic anhydride are diluted in 370 ml of dichloromethane at 20° C. The solution obtained is cooled to 0±2° C. before introducing 2.8 ml of a 96% sulphuric acid solution in a time of about 10 minutes. After stirring for about 10 minutes, 184.2 g (1 mol, 1 eq) of benzhydrol are introduced in portions at 0° C.±2° C. in 60±15 minutes. The reaction medium is maintained in contact for 2 hours at this temperature.

b) Methyl Diphenylmethylthioacetate (MDMTA)

108.3 g (1.02 mol; 1.02 eq) of methyl thioglycolate are introduced at 0° C.±2° C., and then the reaction mixture is heated to 20° C.±2° C. and kept in contact for 2 hours at this temperature.

c) Methyl 2-diphenylmethylsulfinylacetate (MDMSA)

The reaction medium is heated to 30° C.±2° C., and 100.5±0.5 g of a 35% hydrogen peroxide solution are added. The progress of the oxidation reaction is monitored by HPLC. After 25 hours of contact, the reaction is complete (R1 and R2<0.5%).

d) Recovery of MDMSA 150 ml of distilled water are stirred. A 25% aqueous ammonia solution is added so as to bring the pH to 8. The aqueous organic phases are separated, and the aqueous phase is extracted with 2×100 ml of dichloromethane. The organic phases are then combined and concentrated under reduced pressure at a temperature of 70° C. The concentrate obtained crystallizes to give, after grinding, a white powder with a yield of 98.0±0.5%.

Examples 2 and 3

Synthesis of MDMSA on a Pilot Scale (100 l)

Example 2

Synthesis of Crystallized MDMSA a) Benzhydryl Acetate

A solution of acetic anhydride (8.73 kg; 85.5 mol; 1.05 eq) in methylene chloride (40 l) is prepared at 20° C.±2° C. A 96% sulphuric acid solution (225 ml; 4.1 mol; 0.05 eq) is then added with a stirring of 100 revolutions/min, at 0° C.±5° C. in 5 to 10 minutes. The benzhydrol (15 kg; 81.4 mol, 1 eq) is then introduced at 0° C.±2° C. in 1.25 hours. The reaction mixture is stirred for a contact time of 2 hours.

b) Methyl Diphenylmethylthioacetate (MDMTA)

Methyl thioglycolate (8.81 kg; 82.9 mol; 1.02 eq) is introduced at 0° C.±2° C. in about 10 minutes. The reaction mixture is brought to the temperature of 20° C.±2° C. and kept at this temperature for a contact time of 2 hours, with a stirring of 100 revolutions/min.

c) Methyl 2-diphenylmethylsulfinylacetate (MDMSA)

The reaction mixture is then brought to 30° C. before introducing sulphuric acid (450 ml; 8.1 mol; 0.1 eq) with stirring (100 revolutions/min), in about 5 to 10 minutes. A 35% hydrogen peroxide solution (8.19 kg; 84.3 mol; 1.035 eq) is then introduced at 30° C.±2° C. in 1 hour. The contact time is determined by monitoring the reaction by HPLC (cf. Table 1).

d) Recovery of MDMSA

The mixture is cooled to 20° C.±2° C. and then 20 l of water are introduced. After neutralizing the reaction medium by adding a sufficient quantity of $NH_4OH$ so that 8<pH<9, the aqueous and organic phases are separated and the aqueous phase extracted twice with 10 l of methylene chloride. The chlorinated phases are washed with 10 l of water.

The solvent is distilled under atmospheric pressure and then under reduced pressure, at a jacket temperature of 70° C. When the distillation is complete, isopropyl acetate (1.8 vol; 42 l) is added and the whole is cooled to −10° C. After draining and drying under vacuum at 45° C., MDMSA is obtained.

TABLE 1

Yield and quality of the MDMSA and of the intermediate products obtained by this method for trials 1 to 4 (step (ii).

| Trial | Formation of benzhydryl acetate | | Formation of MDMTA | | Formation of MDMSA | | HPLC of the finished product % | Yield % |
|---|---|---|---|---|---|---|---|---|
| | Time | HPLC % | Time | HPLC % | Time | HPLC % | | |
| 1 | 2 h | 98.9 | 2 h | 98.5 | 10 h | T = 1<br>S = 0.3 | D = 99.7<br>S = 0.3 | 88 |
| | | | | | 11 h | T = 0.7<br>S = 0.35 | | |
| | | | | | 11 h 30 | T = 0.3<br>S = 0.4 | | |
| 2 | 2 h | 99.3 | 2 h | 99.1 | 11 h 30 | T = 0.9<br>S = 0.35 | D = 99.6<br>S = 0.3<br>T = 0.1 | 86.4 |
| 3 | 2 h | 99.3 | 2 h | 99.0 | 11 h 30 | T = 0<br>S = 0.4 | D = 99.7<br>S = 0.3 | 90.1 |
| 4 | 2 h | 99.3 | 2 h | 99.1 | 5 h | T = 7.2<br>S = 0.16 | D = 99.7<br>S = 0.3 | 90.0 |

TABLE 1-continued

Yield and quality of the MDMSA and of the intermediate products obtained by this method for trials 1 to 4 (step (ii)).

| Trial | Formation of benzhydryl acetate | | Formation of MDMTA | | Formation of MDMSA | | HPLC of the finished product % | Yield % |
|---|---|---|---|---|---|---|---|---|
|  | Time | HPLC % | Time | HPLC % | Time | HPLC % | | |
|  |  |  |  |  | 6 h 30 | T = 4.4 |  |  |
|  |  |  |  |  |  | S = 0.17 |  |  |
|  |  |  |  |  | 8 h | T = 2.3 |  |  |
|  |  |  |  |  |  | S = 0.22 |  |  |
|  |  |  |  |  | 9 h | T = 1.6 |  |  |
|  |  |  |  |  |  | S = 0.14 |  |  |
|  |  |  |  |  | 10 h | T = 1.15 |  |  |
|  |  |  |  |  |  | S = 0.3 |  |  |
|  |  |  |  |  | 11 h | T = 0.6 |  |  |
|  |  |  |  |  |  | S = 0.38 |  |  |
|  |  |  |  |  | 11 h 30 | T = 0.3 |  |  |
|  |  |  |  |  |  | S = 0.38 |  |  |

D = MDMSA
S = Sulphone
T = MDMTA

These results demonstrate that the production of benzhydryl acetate and of MDMTA can be reproducible.

The formation of MDMSA takes place in 11 h 30 min and reproducibly gives, after crystallization from isopropyl acetate, a final product which is in conformity ($R_1$ and $R_2$<0.5%), with a yield of the order of 90%.

Example 3

Synthesis of Crude MDMSA a) Benzhydryl Acetate

A solution of acetic anhydride (8.73 kg; 85.5 mol; 1.05 eq) in methylene chloride (40 l) is prepared at 20° C. A 96% sulphuric acid solution (225 ml; 4.1 mol; 0.05 eq) is then added with a stirring of 100 revolutions/min, at 0° C.±5° C. in 5 to 10 minutes. The benzhydrol (15 kg; 8.4 mol, 1 eq) is then introduced at 0° C.±2° C. in 1.25 hours. The reaction mixture is stirred for a contact time of 2 hours.

b) Methyl Diphenylmethylthioacetate (MDMTA)

Methyl thioglycolate (8.81 kg; 82.9 mol; 1.02 eq) is introduced at 0° C. in about 10 minutes. The reaction mixture is brought to the temperature of 20° C.±2° C. and kept at this temperature for a contact time of 2 hours, with stirring of 100 revolutions/min.

c) Methyl 2-diphenylmethylsulfinylacetate (MDMSA)

Once the reaction mixture has been brought to 30° C.±2° C., a 35% hydrogen peroxide solution (8.19 kg; 84.3 mol; 1.035 eq) is introduced with stirring (100 revolutions/min) in 1 hour. The contact time is determined by monitoring the reaction by HPLC (cf. Table 2).

d) Recovery of MDMSA

The mixture is cooled to 20° C. and then 20 l of water are introduced. After neutralizing the reaction medium by adding a sufficient quantity of NH$_4$OH so that 8<pH<9, the aqueous and organic phases are separated and the aqueous phase extracted twice with 10 l of methylene chloride. The chlorinated phases are washed with 10 l of water.

The solvent is distilled to dryness under atmospheric pressure and then under reduced pressure at a jacket temperature of 70° C. in a Moritz® turbosphere.

TABLE 2

Yield and quality of the finished product and of the intermediate products for trials 5 and 6

| Trial | Formation of benzhydryl acetate | | Formation of MDMTA | | Formation of MDMSA | | HPLC of the finished product % | Yield % |
|---|---|---|---|---|---|---|---|---|
|  | Time | HPLC % | Time | HPLC % | Time | HPLC % | | |
| 5 | 2 h | 99.6 | 2 h | 99.2 | 35 h | T = 0.3 | D = 99.12 | 97.2 |
|  |  |  |  |  |  | S = 0.4 | S = 0.44 |  |
|  |  |  |  |  |  |  | T = 0.24 |  |
| 6 | 2 h | 99.3 | 2 h | 98.9 | 33 h | T = 0.17 | D = 99.2 | 97 |
|  |  |  |  |  |  | S = 0.4 | S = 0.4 |  |
|  |  |  |  |  |  |  | T = 0.2 |  |

D = MDMSA
S = Sulphone
T = MDMTA

These results show that the steps of formation of benzhydryl acetate and of MDMTA can be reproducible.

The step of oxidation of MDMTA requires a contact time of about 33–35 hours and gives an MDMSA product which is in conformity ($R_1$ and $R_2$<0.5%), with good yields (of the order of 97%).

The invention claimed is:

1. Method for preparing methyl 2-diphenylmethylsulfinylacetate (MDMSA) comprising the steps of:
   (i) conversion of benzhydrol into methyldiphenylmethylthioacetate; and
   (ii) conversion of methyldiphenylmethylthioacetate into methyl-2-diphenylmethylsulfinylacetate.

2. Method according to claim 1, in which step (i) comprises the following steps:
   a1) conversion of benzhydrol to benzhydrol carboxylate in an appropriate solvent;
   b1) conversion of the benzhydrol carboxylate to methyl diphenylmethylthioacetate.

3. Method according to claim 2, in which the step (a1) comprises reacting benzhydrol and an acid anhydride in the presence of an inorganic acid and in an appropriate solvent.

4. Method according to claim 3, in which the solvent is an aprotic solvent.

5. Method according to claim 4, in which the aprotic solvent is chosen from chlorinated solvents, aromatic solvents, hydrocarbon solvents and ethereal solvents.

6. Method according to claim 5, in which the aprotic solvent is chosen from chlorinated solvents.

7. Method according to claim 6, in which the solvent is dichloromethane.

8. Method according to claim 3, in which the acid anhydride is chosen from acetic anhydride, propanoic anhydride and butyric anhydride.

9. Method according to claim 8, in which the acid anhydride is acetic anhydride.

10. Method according to claim 3, in which the inorganic acid is chosen from hydrochloric acid, butyric acid, o-phosphoric acid and sulfuric acid.

11. Method according to claim 10, in which the inorganic acid is sulfuric acid.

12. Method according to claim 3, in which the quantity of inorganic acid used is from 0.02 to 0.3 molar equivalents relative to the benzhydrol.

13. Method according to claim 3, in which the reaction temperature in step a) is between +5° C. and +5° C.

14. Method according to claim 2, in which step b1) comprises bringing the solution obtained in step a) into contact with methyl thioglycolate.

15. Method according to claim 14, in which the contact time used in step b1) is between 2 and 3 hours.

16. Method according to claim 14, in which the contact temperature used in step b1) is between 15° C. and 25° C.

17. Method according to claim 1, in which the oxidizing agent is chosen from oxone, potassium permanganate, sodium percarbonate, and peroxides.

18. Method according to claim 17, in which the oxidizing agent is hydrogen peroxide.

19. Method according to claim 18, in which the hydrogen peroxide is added in the form of a 35% aqueous solution.

20. Method according to claim 1, in which the oxidizing agent is used in an amount of 1 to 1.1 molar equivalent.

21. Method according to claim 1, in which the reaction temperature in step (ii) is between 28° C. and 37° C.

22. Method according to claim 3, in which an additional quantity of inorganic acid is added in step (ii).

23. Method according to claim 22, in which the additional quantity of inorganic acid is from 0.02 to 0.3 molar equivalents.

24. Method according to claim 22, in which the contact time in step (ii) is between 10 and 13 hours.

25. Method according to claim 1, which comprises an additional step (iii) recovering the methyl 2-diphenyl-methylsulfinylacetate obtained.

26. Method according to claim 25, in which step (iii) comprises a distillation of the solvent to dryness.

27. Method according to claim 25, in which step (iii) comprises a step of direct crystallization.

28. Method according to claim 27, in which the crystallization solvent is chosen from methanol, ethanol, ethyl acetate, isopropyl acetate and toluene.

29. Method according to claim 28, in which the crystallization solvent is isopropyl acetate.

30. Method according to claim 1, in which the successive steps are carried out in the same reactor without isolation of the intermediate compounds.

31. Method for preparing modafinil comprising preparing MDMSA according to claim 1.

* * * * *